United States Patent
Blackford

(10) Patent No.: US 10,827,743 B2
(45) Date of Patent: Nov. 10, 2020

(54) MOSQUITO BREEDING PREVENTION DEVICE AND SYSTEM

(71) Applicant: William Jeffrey Blackford, Evansville, IN (US)

(72) Inventor: William Jeffrey Blackford, Evansville, IN (US)

(*) Notice: Subject to any disclaimer, the term of this patent is extended or adjusted under 35 U.S.C. 154(b) by 69 days.

(21) Appl. No.: 15/892,064

(22) Filed: Feb. 8, 2018

(65) Prior Publication Data

US 2018/0228141 A1 Aug. 16, 2018

Related U.S. Application Data

(60) Provisional application No. 62/457,322, filed on Feb. 10, 2017.

(51) Int. Cl.
*A01M 29/34* (2011.01)
*E04D 13/064* (2006.01)
*E04D 13/08* (2006.01)

(52) U.S. Cl.
CPC ......... *A01M 29/34* (2013.01); *E04D 13/0645* (2013.01); *A01M 2200/012* (2013.01); *E04D 2013/086* (2013.01); *E04D 2013/0813* (2013.01)

(58) Field of Classification Search
CPC ............ A01M 29/34; A01M 2200/012; E04D 13/0645; E04D 2013/086
USPC ............ 52/12, 16; 210/459, 162, 483, 510.1
See application file for complete search history.

(56) References Cited

U.S. PATENT DOCUMENTS

| | | | |
|---|---|---|---|
| 3,793,237 A * | 2/1974 | Watkinson | C08G 18/48 521/107 |
| 4,470,908 A | 9/1984 | Odekirk | |
| D301,164 S | 5/1989 | Weaver | |
| 5,159,789 A * | 11/1992 | Haapanen | E04D 13/08 52/12 |
| D351,898 S | 10/1994 | Stowers, Jr. | |
| 6,584,733 B2 | 7/2003 | Wade | |
| 6,708,443 B2 | 3/2004 | Hall | |
| 7,200,969 B2 * | 4/2007 | Rotter | E04D 13/076 210/162 |
| 7,407,574 B2 | 8/2008 | Robinson | |
| D617,427 S | 6/2010 | McNamara | |

(Continued)

FOREIGN PATENT DOCUMENTS

| AU | 2007100822 | 9/2007 |
|---|---|---|
| CN | 203891181 | 10/2014 |

(Continued)

*Primary Examiner* — Joshua K Ihezie
(74) *Attorney, Agent, or Firm* — Martin IP Law Group; C. Richard Martin

(57) ABSTRACT

A device for insertion into an open end of a length of pipe to prevent mosquitoes from entering the pipe is provided. The device includes a piece of flexible foam material having a front face, a rear face and one or more edges joining the front face to the rear face. A plurality of indentions, preferably three, are formed in the front face of the piece of flexible foam material to allow a user to quickly and easily grip the device to insert or remove it from the pipe. The piece of flexible foam material preferably comprises open cell foam sized to permit water to flow through while preventing insects from passing through. The device may be used in connection with a system to prevent mosquitoes from entering into a rain gutter drain extension or a rain barrel system.

3 Claims, 4 Drawing Sheets

(56) References Cited

U.S. PATENT DOCUMENTS

| | | | |
|---|---|---|---|
| 8,220,206 B2 | 7/2012 | Konkey | |
| 8,397,746 B1* | 3/2013 | Taborek | E04D 13/08 |
| | | | 137/357 |
| 2004/0040598 A1* | 3/2004 | Zimmerman, Jr. | E03B 1/04 |
| | | | 137/357 |
| 2004/0223807 A1* | 11/2004 | Bevilacqua | F16L 9/003 |
| | | | 404/7 |
| 2005/0145560 A1* | 7/2005 | Jones | E04D 13/076 |
| | | | 210/459 |
| 2005/0160681 A1* | 7/2005 | Boelling | E04D 13/08 |
| | | | 52/16 |
| 2005/0178072 A1* | 8/2005 | Olthoff | E04D 13/002 |
| | | | 52/12 |
| 2005/0263480 A1* | 12/2005 | Smolko | A45F 3/20 |
| | | | 215/308 |
| 2006/0016129 A1* | 1/2006 | Riese | E04D 13/08 |
| | | | 52/16 |
| 2008/0229673 A1* | 9/2008 | LaMorte | E04D 13/08 |
| | | | 52/12 |
| 2010/0170837 A1* | 7/2010 | Konkey | E04D 13/076 |
| | | | 210/162 |
| 2010/0199574 A1 | 8/2010 | Perlatti | |
| 2011/0005602 A1* | 1/2011 | Harrington | E03B 1/04 |
| | | | 137/1 |
| 2011/0088791 A1* | 4/2011 | Primm, Jr. | E04D 13/08 |
| | | | 137/356 |
| 2011/0203191 A1* | 8/2011 | Argentina | E04D 13/0645 |
| | | | 52/12 |
| 2012/0247031 A1 | 10/2012 | Konkey | |
| 2013/0145699 A1* | 6/2013 | Olthoff | E04D 13/076 |
| | | | 52/12 |
| 2016/0040820 A1* | 2/2016 | Morris | F15D 1/04 |
| | | | 138/39 |
| 2016/0281364 A1* | 9/2016 | Lolio, Jr. | E04D 13/08 |

FOREIGN PATENT DOCUMENTS

| | | |
|---|---|---|
| JP | 005378872 | 12/2013 |
| JP | 02017089355 A | 5/2017 |

* cited by examiner

MOSQUITO BREEDING PREVENTION DEVICE AND SYSTEM

BACKGROUND OF THE INVENTION

Field of the Invention

The present invention relates to systems and devices for preventing insects from entering into a system for transferring liquid from one location to another. More specifically, the present invention relates to a device for insertion into an open end of a length of pipe to prevent insects such as mosquitoes from entering the pipe.

Description of the Related Art

Rain gutter drain extensions can accumulate and hold water for extended periods of time. Mosquitoes have access to this water for breeding through both the gutter drain inlet and the drain extension outlet. Rain barrels allow access to mosquitoes for breeding through the gutter drain inlet, if not properly screened, and through the overflow tube. The accumulated water is a prime breeding site for disease carrying mosquitoes in both rain water systems.

Accordingly, there is a need for a device and system that prevents mosquitoes from gaining access to standing water in rain gutter extensions and/or rain barrels thereby denying them access to prime breeding sites. There is also a need to allow water to freely pass through the rain gutter extension and/or rain barrel while still preventing access by mosquitoes.

SUMMARY OF THE INVENTION

It is therefore an object of the present invention to provide a device that can be quickly and easily inserted into the inlet and/or outlet of a system for transferring liquid to prevent mosquitoes from gaining access to standing water within the system for breeding.

It is also an object of the invention to provide a system for preventing insects from entering into a system for transferring liquid from one location to another, such as a rain barrel or rain gutter drain extension.

The present invention meets these objects by providing a generally circular piece of plastic foam material that can be quickly and easily placed at the inlet and/or outlet of a rain gutter drain extension. If there is no access to the drain extension inlet, or if preferred, the foam element can be placed in the gutter drain outlet. For rain barrels, the foam element is removably placed in the gutter drain outlet, if not properly screened, and in the outlet of the overflow drain tube. Indentations are located on the front of the plastic foam material to provide a method to grip for installation and removal. The foam material is open pore, flexible foam such as polyether foam of about 10-20 cells per square inch. The foam allows rainwater to travel through the drain extensions while preventing mosquitoes access to the accumulated water.

According to one presently preferred embodiment of the invention, there is provided a device for insertion into an open end of a length of pipe to prevent insects from entering the pipe. The device includes a piece of flexible foam material having a front face, a rear face and one or more edges joining the front face to the rear face. The device further includes gripping means for a user to readily grip the front face of the piece of flexible foam material to insert or remove the piece of flexible foam material from the open end of the length of pipe.

According to one preferred embodiment of the invention, the gripping means comprises a plurality of indentions, preferably three, in the front face of said piece of flexible foam material. The piece of flexible foam material preferably comprises open cell foam, which may, according to one presently preferred embodiment, be polyether plastic. The open cells are sized to permit water to flow through while preventing insects from passing through. According to one preferred embodiment, the open cells range in size from 10 cells per square inch to 20 cells per square inch. The front face and rear face of the piece of flexible foam material may be circular in shape with a singular, continuous edge connecting the front face to the rear face.

A further aspect of the invention is a device for insertion into an open end of a length of pipe to prevent insects from entering the pipe comprising a piece of open cell flexible foam material having a front face, a rear face and one or more edges joining said front face to said rear face, wherein the open cells in the piece of foam are sized to permit water to flow through while preventing insects from passing through. The piece of flexible foam material may further include a plurality of indentions, preferably three (3), in the front face thereof permitting a user to readily grip the front face of the piece of flexible foam material to insert or remove the piece of flexible foam material from the open end of the length of pipe. The open cell foam may be polyether plastic. The open cells preferably range in size from 10 cells per square inch to 20 cells per square inch. The front face and rear face may be circular in shape and a singular, continuous edge may connect the front face to the rear face.

Yet a further aspect of the present invention is a system for preventing insects from entering into a system for transferring liquid from one location to another. This system includes a drain inlet opening in a first end of the system for transferring liquid from one location to another, a drain outlet opening in a second end of the system for transferring liquid from one location to another, and a piece of flexible foam material having a front face, a rear face and one or more edges joining the front face to the rear face. Gripping means may also be provided for a user to readily grip the front face of the piece of flexible foam material to insert or remove the piece of flexible foam material from the open end of the length of pipe.

The piece of flexible foam material may be removably positioned in one of the inlet opening or the outlet opening. According to one embodiment of the invention, a second piece of flexible foam material is removably positioned in the other of the inlet opening or the outlet opening.

A further aspect of the invention provides that the system for transferring liquid comprises a drain extension pipe with a first piece of flexible foam material removably positioned in an inlet opening therein and a second piece of flexible foam material removably positioned in an outlet opening therein.

Alternatively, the system for transferring liquid may comprise a rain gutter having a drain outlet connected to a drain inlet of a downspout pipe; a drain extension pipe having an inlet opening connected to an outlet of the downspout, and an outlet opening; a first piece of flexible foam material removably positioned in the drain outlet of the rain gutter; and a second piece of flexible foam material removably positioned in the outlet opening of the drain extension pipe.

According to yet a further embodiment of the invention, the system for transferring liquid comprises a rain gutter having a drain outlet connected to a drain inlet of a downspout pipe; a rain barrel having an inlet opening connected to an outlet of the downspout pipe, and an overflow outlet opening; an overflow tube having an inlet opening connected to the overflow outlet opening of the rain barrel; a first piece of flexible foam material removably positioned in the drain outlet of the rain gutter; and a second piece of flexible foam material removably positioned in an outlet opening of the overflow tube.

These and other objects, features and advantages of the present invention will become apparent from a review of the following drawings and detailed description of the preferred embodiments of the invention.

BRIEF DESCRIPTION OF THE DRAWINGS

The present invention can best be understood in connection with the accompanying drawings. It is noted that the invention is not limited to the precise embodiments shown in the drawings, in which.

DETAILED DESCRIPTION OF THE INVENTION

Figure 1:
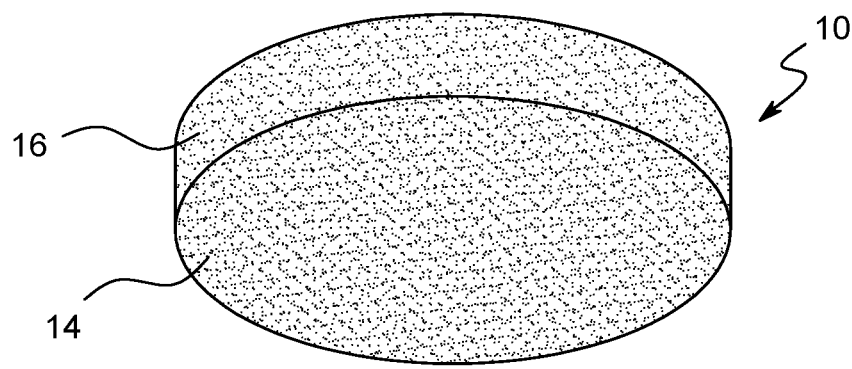
FIG. 1 is a bottom prospective view of a device for insertion into an open end of a length of pipe to prevent insects from entering the pipe according to a preferred embodiment of the present invention.

For purposes of promoting and understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

Figure 2:
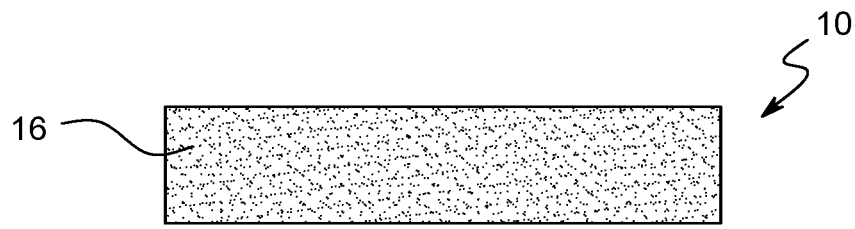
FIG. 2 is a side plan view of the device shown in FIG. 1.
Figure 3:
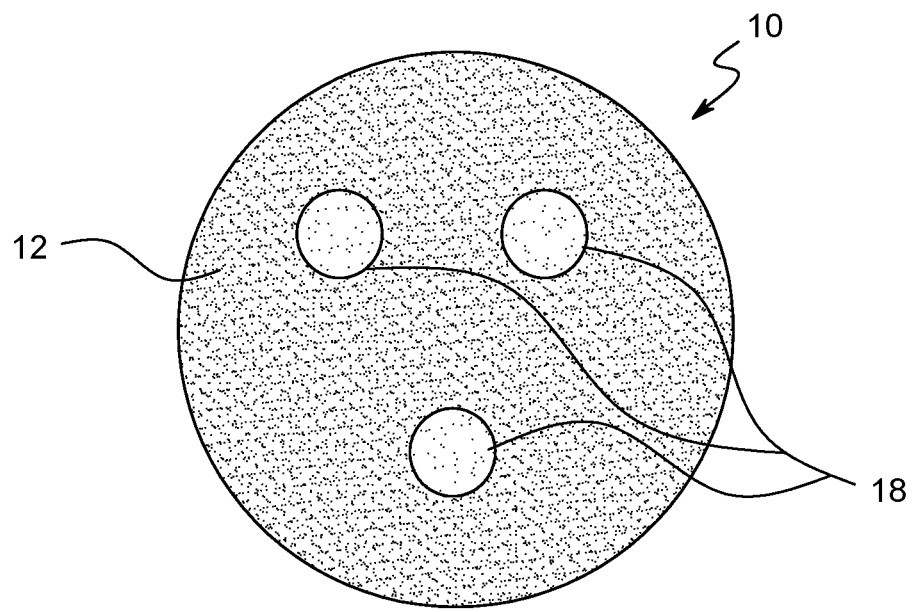
FIG. 3 is a top plan view of the device shown in FIG. 1 and FIG. 2.

As best shown in FIG. 1 and FIG. 2, one presently preferred embodiment of the invention comprises a rain gutter drain extension and rain barrel foam element 10 generally comprised of a circular piece of flexible, open pore foam material having a front face 12, and a rear face 14 connected by a continuous edge or sidewall 16. As shown in FIG. 3, the front face 12 of the foam element 10 includes a plurality of indentations 18 to provide a method to grip the foam element 10 for installation and removal.

The diameter of the foam element 10 should be slightly larger than the inner diameter of the pipe into which it is to be inserted in order to provide an effective barrier. For typical residential rain gutter applications, a foam element 10 having a diameter of about 5 inches and a thickness of around 2.5 inches is preferred. Although other materials are contemplated and within the spirit and scope of the invention, the open cell foam material of the foam element 10 accordingly to one presently preferred embodiment is polyether plastic. The open cells of the foam element 10 may be of any size that permits an adequate flow of liquid and small materials to pass therethrough while being small enough to prevent insects such as mosquitoes from passing through and gaining access to the standing water to breed. According to one preferred embodiment of the invention, the cells range in size from 10 cells per square inch to 20 cells per square inch. The foam element 10 is flexible, easily cut and can be easily removed from or inserted into a drain inlet or drain outlet to be cleaned and replaced if the need occurs.

Figure 4:
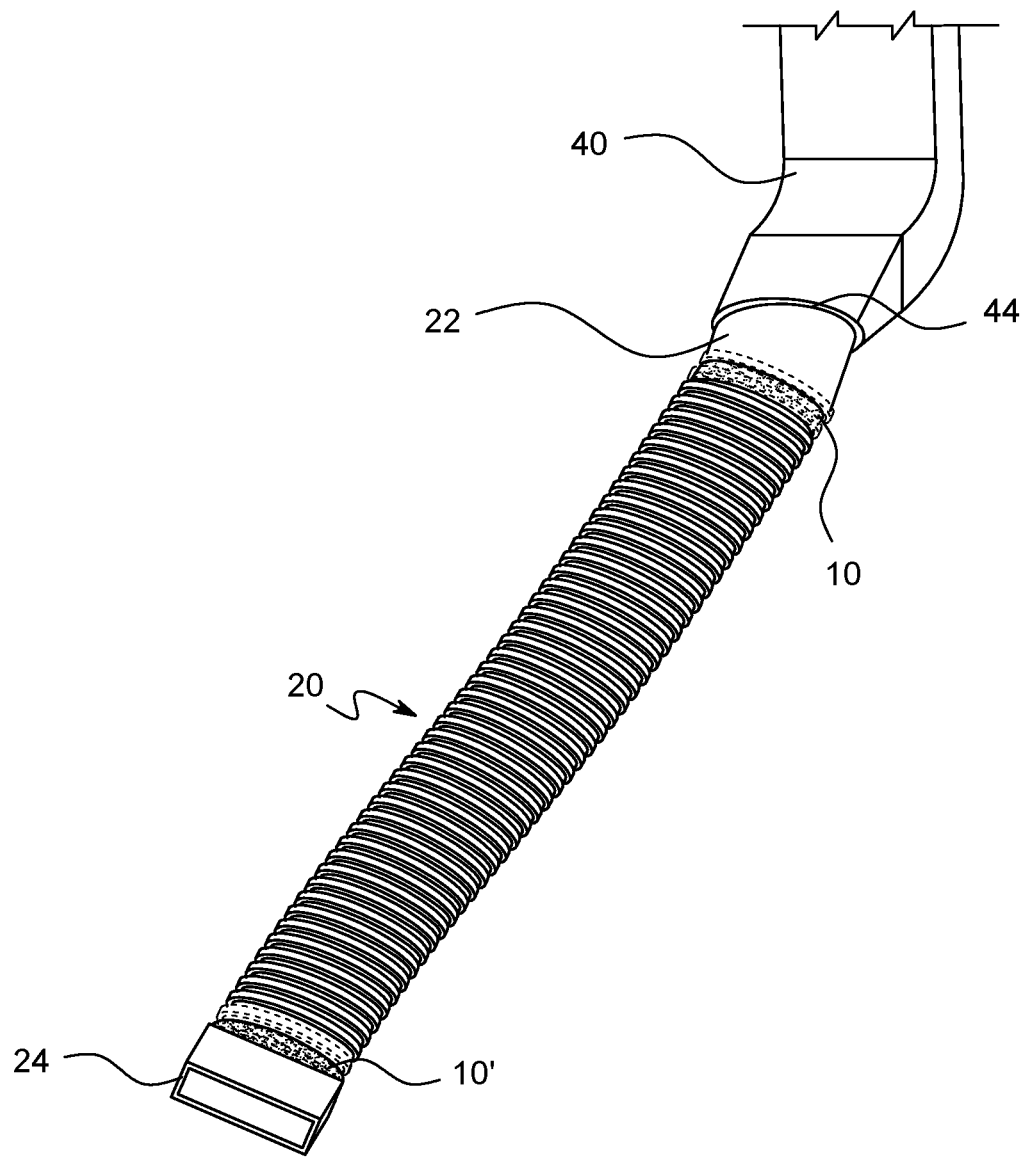
FIG. 4 is a perspective view of a system for preventing insects from entering into a system for transferring liquid from one location to another using the device shown in FIGS. 1-3 according to one preferred embodiment of the present invention.
Figure 5:
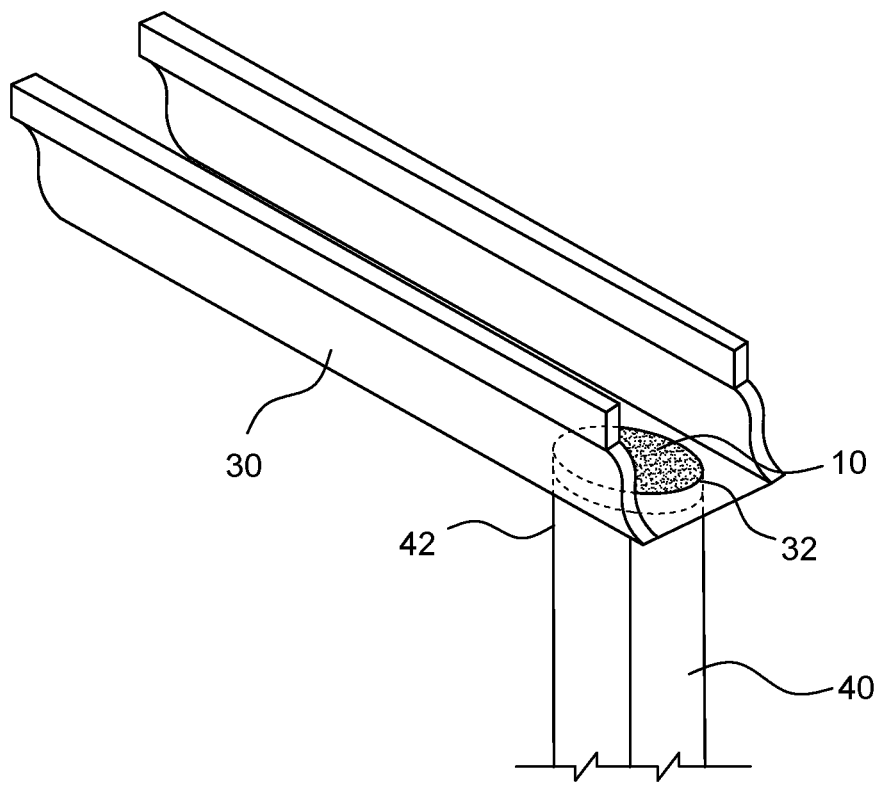
FIG. 5 is a perspective view of the inlet part of a system for preventing insects from entering into a system for transferring liquid from one location to another using the device shown in FIGS. 1-3 according to an alternative embodiment of the present invention.

In a typical installation, as shown in FIG. 4, foam elements 10, 10' are removably installed in the inlet 22 and outlet 24 of a drain extension pipe 20, respectively. Where there is no easy access to the inlet 22 of the drain extension pipe 20, the inlet-side foam element 10 may be installed in the drain outlet 32 of a rain gutter 30, which connects to a downspout pipe 40, as shown in FIG. 5. The inlet 42 of the downspout pipe 40 is connected to the drain outlet 32 of the rain gutter 30 while the outlet 44 of the downspout pipe is connected to the inlet 22 of the drain extension pipe 20 (FIG. 4).

Figure 6:
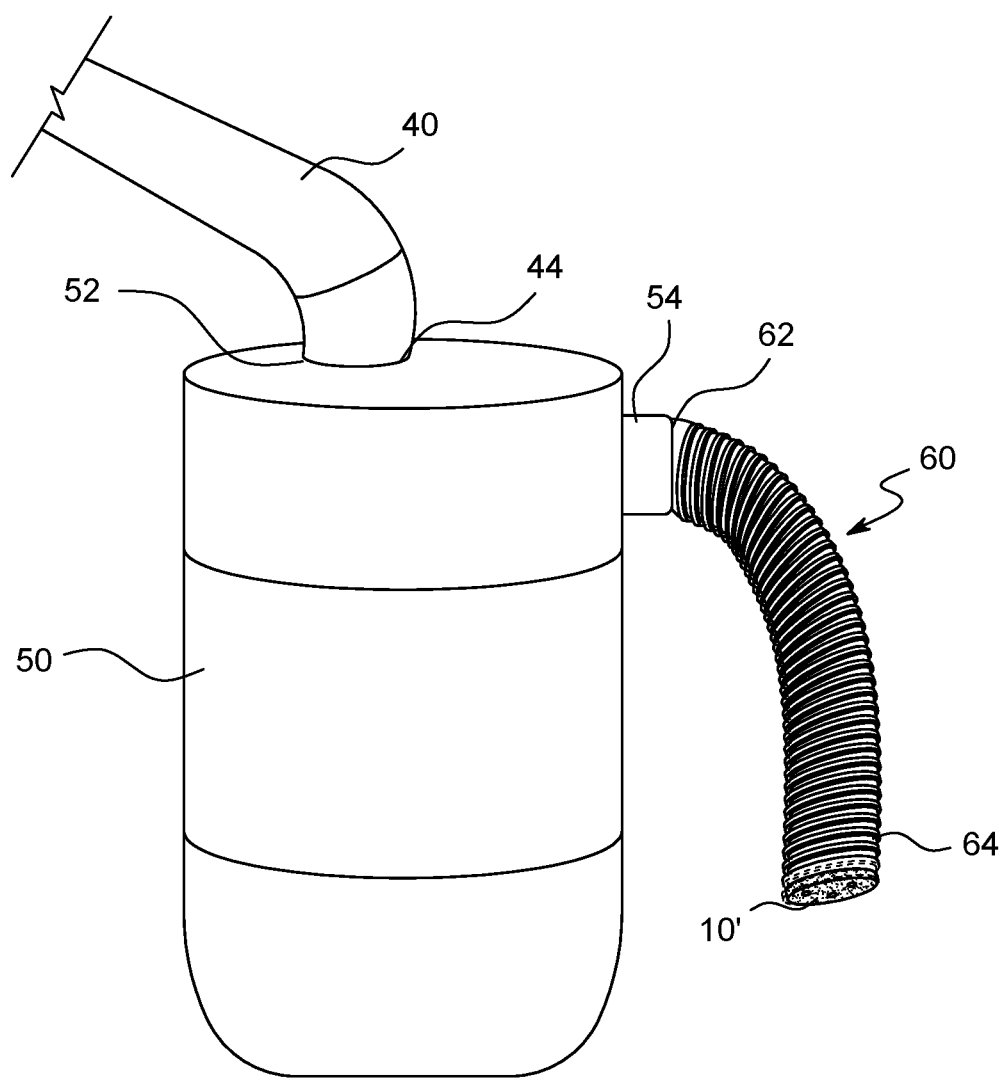
FIG. 6 is a perspective view of the outlet part of a system for preventing insects from entering into a system for transferring liquid from one location to another using the device shown in FIGS. 1-3 according to an alternative embodiment of the present invention.

The system may also be used in conjunction with a rain barrel 50 for rainwater retention as shown in FIG. 6. The rain barrel 50 has an inlet 52 connected to the outlet 44 of the downspout pipe 40, and an overflow drain outlet 54 located in a sidewall thereof near the top of the barrel 50. The overflow drain outlet 54 may be connected to the inlet 22 of a drain extension pipe 20 to divert overflow rainwater away from the barrel 50 and the structure. To prevent mosquitoes from entering the rain barrel 50 and having access to the water therein for breeding, a first foam element 10 may be installed in the drain outlet 32 of a rain gutter 30, which connects to a downspout pipe 40, as shown in FIG. 5. A second foam element 10' may be inserted into the outlet 64 of an overflow tube 60 to prevent mosquitoes from entering the rain barrel 50 through the open outlet 64.

A foam element 10 inserted on the upstream side of the system for transferring liquid, as shown in FIG. 4 has the additional benefit of preventing larger debris from entering into the system.

This detailed description, and particularly the specific details of the exemplary embodiment disclosed, is given primarily for clearness of understanding and no unnecessary limitations are to be understood therefrom, for modifications will become evident to those skilled in the art upon reading this disclosure and may be made without departing from the spirit or scope of the claimed invention.

I claim:

1. A system for preventing insects from entering into a drain extension pipe, said system comprising:
   a drain inlet opening in a first end of the drain extension pipe;
   a drain outlet opening in a second end of the drain extension pipe;
   a first piece of flexible foam material having a front face, a rear face and one or more edges joining said front face to said rear face, said first piece of flexible foam material being removably positioned in said inlet opening, wherein the entire length of said one or more edges of said first piece of flexible foam material engage an inner surface of said inlet opening;
   a second piece of flexible foam material having a front face, a rear face and one or more edges joining said front face to said rear face, said second piece of flexible foam material being removably positioned in said outlet opening, wherein the entire length of said one or more edges of said second piece of flexible foam material engage an inner surface of said outlet opening.

2. A system for preventing insects from entering into a system for transferring liquid from one location to another, said system comprising:
- a rain gutter having a drain outlet connected to a drain inlet of a downspout pipe;
- a drain extension pipe having an inlet opening connected to an outlet of the downspout, and an outlet opening;
- a first piece of flexible foam material having a front face, a rear face and one or more edges joining said front face to said rear face, said first piece of flexible foam material being removably positioned in the drain outlet of the rain gutter, wherein the piece of flexible foam material further includes a plurality of indentions in the front face thereof for a user to readily grip the front face of said first piece of flexible foam material to insert or remove the first piece of flexible foam material from said drain outlet of the rain gutter; and
- a second piece of flexible foam material having a front face, a rear face and one or more edges joining said front face to said rear face, said second piece of flexible foam material being removably positioned in the outlet opening of said drain extension pipe, wherein the second piece of flexible foam material further includes a plurality of indentions in the front face thereof for a user to readily grip the front face of said second piece of flexible foam material to insert or remove the second piece of flexible foam material from said outlet opening of said drain extension pipe.

3. A system for preventing insects from entering into a rain gutter and rain barrel assembly, said system comprising:
- a rain gutter having a drain outlet connected to a drain inlet of a downspout pipe;
- a rain barrel having an inlet opening connected to an outlet of the downspout pipe, and an overflow outlet opening;
- an overflow tube having an inlet opening connected to the overflow outlet opening of the rain barrel;
- a first piece of flexible foam material having a front face, a rear face and one or more edges joining said front face to said rear face, said piece of flexible foam material being removably positioned in the drain outlet of the rain gutter, wherein the entire length of said one or more edges of said piece of flexible foam material engage an inner surface of said drain outlet of the rain gutter; and
- a second piece of flexible foam material having a front face, a rear face and one or more edges joining said front face to said rear face, said piece of flexible foam material being removably positioned in an outlet opening of said overflow tube, wherein the entire length of said one or more edges of said piece of flexible foam material engage an inner surface of said outlet opening of said overflow tube.

* * * * *